US011897861B2

(12) United States Patent
Rudolf et al.

(10) Patent No.: US 11,897,861 B2
(45) Date of Patent: Feb. 13, 2024

(54) METHOD FOR THE PREPARATION OF COMPOUNDS WITH CYCLIC MONOTHIOCARBONATE GROUPS

(71) Applicant: BASF SE, Ludwigshafen am Rhein (DE)

(72) Inventors: Peter Rudolf, Ludwigshafen (DE); Indre Thiel, Ludwigshafen (DE); Markus Jegelka, Ludwigshafen (DE); Bernd Bruchmann, Ludwigshafen (DE); Elliot Christ, Freiburg (DE)

(73) Assignee: BASF SE, Ludwigshafen am Rhein (DE)

( * ) Notice: Subject to any disclaimer, the term of this patent is extended or adjusted under 35 U.S.C. 154(b) by 153 days.

(21) Appl. No.: 17/310,075

(22) PCT Filed: Jan. 17, 2020

(86) PCT No.: PCT/EP2020/051115
§ 371 (c)(1),
(2) Date: Jul. 15, 2021

(87) PCT Pub. No.: WO2020/148423
PCT Pub. Date: Jul. 23, 2020

(65) Prior Publication Data
US 2021/0380553 A1 Dec. 9, 2021

(30) Foreign Application Priority Data
Jan. 18, 2019 (EP) .................... 19152435

(51) Int. Cl.
C07D 327/04 (2006.01)
(52) U.S. Cl.
CPC .................. C07D 327/04 (2013.01)
(58) Field of Classification Search
CPC .................................................. C07D 327/04
See application file for complete search history.

(56) References Cited

U.S. PATENT DOCUMENTS

| | | | |
|---|---|---|---|
| 2,828,318 A | 3/1958 | Reynolds | |
| 3,072,676 A | 1/1963 | Johnson et al. | |
| 3,201,416 A | 8/1965 | Johnson et al. | |
| 3,349,100 A | 10/1967 | Villa | |
| 3,517,029 A | 6/1970 | Johnson | |
| 5,378,728 A | 1/1995 | Nadelson et al. | |

FOREIGN PATENT DOCUMENTS

| | | |
|---|---|---|
| CN | 1505622 A | 6/2004 |
| CN | 102548985 A | 7/2012 |
| CN | 103130764 A | 6/2013 |
| CN | 105283448 A | 1/2016 |
| CN | 105481842 A | 4/2016 |
| CN | 106459356 A | 2/2017 |
| EP | 0347840 A2 | 12/1989 |
| EP | 1471053 A2 | 10/2004 |
| EP | 2468791 A1 | 6/2012 |
| JP | 2007-178903 A | 7/2007 |
| WO | WO-2019/034469 A1 | 2/2019 |

OTHER PUBLICATIONS

PubChem CID 14024148, National Center for Biotechnology Information. PubChem Compound Summary for CID 14024148, 1,3-Oxathiolan-2-one, 5-(chloromethyl)-. https://pubchem.ncbi.nlm.nih.gov/compound/1_3-Oxathiolan-2-one_-5-_chloromethyl. Accessed May 9, 2023, create date Feb. 9, 2007. (Year: 2007).*
Dibenedetto et al., "Converting wastes into added value products: from glycerol to glycerol carbonate, glycidol and epichlorohydrin using environmentally friendly synthetic routes", Tetrahedron, vol. 67, 2011, pp. 1308-1313.
Bej, et al., "Glutathione Triggered Cascade Degradation of an Amphiphilic Poly(disulfide)-Drug Conjugate and Targeted Release", Bioconjugate Chemistry, vol. 30, Issue 1. Dec. 17, 2018, pp. 101-110.
Etlis, et al., "The reaction of chloro derivatives of alkene thiocarbonates with ammonia and with amines", Doklady Physical Chemistry—Doklady Academii Nauk USSR, vol. 142, Issue 1-6, 1962 , pp. 101-103.
International Search Report for PCT Patent Application No. PCT/EP2020/051115, dated Mar. 9, 2020, 4 pages.
Kong, et al., "Highly Selective Fluorescent Probe for Imaging H2Se in Living Cells and in Vivo Based on the Disulfide Bond", Analytical Chemistry, vol. 89, Issue 1, Dec. 5, 2016, pp. 688-693.
Luo, et al., "Synthesis of cyclic monothiocarbonates via the coupling reaction of carbonyl sulfide (COS) with epoxides", Catalysis Science & Technology , vol. 6, Issue 1, Aug. 17, 2015, pp. 188-192.
Nishiyama, et al., "A facile method for the synthesis of 1,3-oxathiolan-2-ones by reaction of oxiranes, sulfur, and carbon monoxide", Tetrahedron, vol. 62, Issue 24, Jun. 12, 2006, pp. 5803-5807.

(Continued)

Primary Examiner — Laura L Stockton
(74) Attorney, Agent, or Firm — Grüneberg and Myers PLLC

(57) ABSTRACT

A process prepares a compound containing at least one cyclic monothiocarbonate group, wherein a salt of an acidic compound with at least one acidic hydrogen atom is reacted with a compound of formula (I),

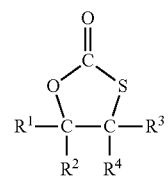

wherein one of the groups $R^1$ to $R^4$ is a group of formula (II), -A-X, with A representing an organic group with at least one carbon atom and X representing a halide, and the remaining groups $R^1$ to $R^4$ independently from each other represent hydrogen or an organic group with 1 to 50 carbon atoms.

14 Claims, No Drawings

(56) References Cited

OTHER PUBLICATIONS

Paquette, et al., "The Alleged Functionalized Episulfones of Etlis", The Journal of Organic Chemistry, vol. 31, Issue 6, Jun. 1, 1966, pp. 1997-1999.
Uenishi, et al., "Intramolecular ring opening of a 2, 3epoxy alcohol by a xanthate anionic center; stereospecific preparation of 2mercapto1, 3diol units", Heteroatom Chemistry, vol. 5, Issue 1, Feb. 1994, pp. 51-60.
Yoichi, et al., "The Reaction of Oxiranes with Carbon Disulfide under High Pressure", Bulletin of the Chemical Society of Japan, vol. 61, Issue 3, Mar. 1988, pp. 921-925.

\* cited by examiner

METHOD FOR THE PREPARATION OF COMPOUNDS WITH CYCLIC MONOTHIOCARBONATE GROUPS

CROSS-REFERENCE TO RELATED APPLICATIONS

This application is the National Stage entry under § 371 of International Application No. PCT/EP2020/051115, filed on Jan. 17, 2020, and which claims the benefit of priority to European Application No. 19152435, filed on Jan. 18, 2019.

BACKGROUND OF THE INVENTION

Field of the Invention

Object of the present invention is a process for the preparation of compounds comprising at least one cyclic monothiocarbonate group, wherein the salt of an acidic compound with at least one acidic hydrogen atom is reacted with a compound of formula (I)

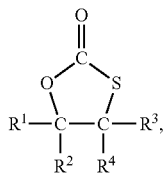

wherein
one of the groups $R^1$ to $R^4$ is a group of formula (II)

-A-X with A representing an organic group with at least one carbon atom and X representing a halide, and the remaining groups $R^1$ to $R^4$ independently from each other represent hydrogen or an organic group with from 1 to 50 carbon atoms.

Description of Related Art

Monothiocarbonate groups provide thiol groups via a ring opening reaction with amino compounds. Thiol groups have high reactivity. Chemical compounds with thiol groups are useful starting materials for chemical synthesis. Polymers with thiol groups can easily be cross-linked or be further modified by chemical reactions. Monothiocarbonate groups are latent thiol groups providers. They provide the thiol groups via the ring opening reaction exactly when required.

Hence, compounds with monothiocarbonate groups are very useful in chemical synthesis and technical applications of chemical compounds such as polymers.

Different methods for the synthesis of compounds with monothiocarbonate groups are described in the state of the art.

According to the process disclosed in U.S. Pat. No. 3,349,100 alkylene monothiocarbonates are obtained by reacting an epoxide with carbonyl sulfide. The availability of carbonyl sulfide is limited. Yields and selectivities of alkylene monothiocarbonates obtained are low.

A synthesis using phosgene as starting material is known from U.S. Pat. No. 2,828,318. Phosgene is reacted with hydroxymercaptanes. Yields of monothiocarbonates are still low, and by-products from polymerization are observed.

Object of U.S. Pat. Nos. 3,072,676 and 3,201,416 is a two-step-process for the preparation of ethylene monothiocarbonates. In a first step mercaptoethanol and chlorocarboxylates are reacted to give hydroxyethylthiocarbonate, which is heated in the second step in the presence of a metal salt catalyst to the ethylene monothiocarbonate.

According to U.S. Pat. No. 3,517,029 alkylene monothiocarbonates are obtained by reacting mercaptoethanol and a carbonate diester in the presence of a catalytically active salt of thorium.

Yoichi Taguchi et al., Bull. Chem. Soc. Jpn., 1988, 61, 921-925 disclose the formation of monothiocarbonate by reacting carbon disulfide and 2,2-dimethyloxirane in the presence of trimethylamine.

Yutaka Nishiyama et al., Tetrahedron, 2006, 62, 5803-5807 disclose the formation of monothiocarbonate using epoxide, sulfur and carbon monoxide as reactants in the presence of sodium hydride.

M. Luo, X.-H. Zhang and D. J. Darensbourg, Catalysis Science & Technology, 2015, article accepted on Aug. 13, 2015 (DOI: 10.1039/c5cy00977d) disclose some specific cyclic monothiocarbonates obtained via coupling reaction of carbonyl sulfides with epoxides.

Etlis, V. S. and Razuvaev, G. A., Doklady Akademi Nauk SSSR, 1962, 142, 838-840 disclose a compound comprising a cyclic monothiocarbonate which is substituted by a secondary amino group and the synthesis thereof. However, according to L. A. Paquette and L. S. Wittenbrook, 1966, 31, 1997-1999, an amino-substituted cyclic monothiocarbonate is not prepared, but a 3-thietane carbamate.

WO 2019/034469 A1 relates to a process for the synthesis of a compound with at least one monothiocarbonate group by reacting a compound with at least one epoxy group with phosgene and subsequently reacting the adduct obtained with an anionic sulfur compound.

The processes of the prior art are processes for the formation of the monothiocarbonate ring system. Such processes are complicated and often require the use of harmful materials such as phosgene.

There is a demand to have an easy process to introduce monothiocarbonate functionality in other chemical compounds, including polymers. Such process should be easy to perform, should be economic and should not involve the use or formation of any harmful materials.

SUMMARY OF THE INVENTION

Accordingly, a process for the preparation of a compound comprising at least one five-membered cyclic monothiocarbonate group has been found.

In a first aspect, the invention relates to a process for the preparation of compounds comprising at least one cyclic monothiocarbonate group, wherein the salt of an acidic compound with at least one acidic hydrogen atom is reacted with a compound of formula (I)

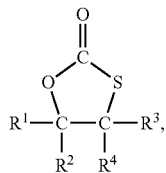

wherein
one of the groups $R^1$ to $R^4$ is a group of formula (II)

-A-X with A representing an organic group with at least one carbon atom and X representing a halide, and the remaining groups $R^1$ to $R^4$ independently from each other represent hydrogen or an organic group with 1 to 50 carbon atoms.

In a further aspect, the invention relates to compounds obtainable by reacting the salt of an acidic compound selected from hydrogen sulfide or an organic compound comprising at least one thiol group with a compound of formula (III)

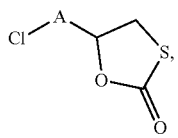

wherein A is an organic group with at least one carbon atom.

In a further aspect, the invention relates to compounds obtainable by reacting the salt of an organic compound comprising at least one imide group with a compound of formula (III)

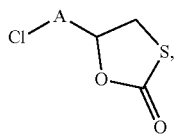

wherein A is an organic group with at least one carbon atom, preferably an alkylene group with 1 to 10 carbon atoms.

DETAILED DESCRIPTION OF THE INVENTION

To the salt of the acidic compound with at least one acidic hydrogen atom Compounds with an acidic hydrogen atom form salts with a base. The acidic hydrogen dissociates from the compound and adds to the base resulting in a salt comprising the organic compound as anion and the base as cation.

Acidic hydrogens are, for example, the hydrogen atoms of hydrogen sulfide ($H_2S$) or the hydrogen atoms of a hydroxy group, a thiol group, an imide group, a carboxylic acid group or an acidic carbon-hydrogen group.

Preferably, the acidic compound is hydrogen sulfide or an organic compound with at least one group selected from a hydroxy group (—OH), a thiol group (—SH), an imide group ((—C(=O)—)$_2$NH), a carboxylic acid group (—COOH) or an acidic carbon-hydrogen group. Acidic carbon-hydrogen groups are particularly those wherein at least one, preferably both, of the two other substituents to the carbon atom of the acid carbon-hydrogen group are electronegative groups, such as carbonyl or carboxylic groups.

More preferably, the acidic compound is an organic compound with at least one group selected from a hydroxy group (—OH), a thiol group (—SH), an imide group ((—C(=O)—)$_2$NH) or a carboxylic acid group (—COOH).

In a most preferred embodiment, the acidic compound is an organic compound with at least one group selected from an imide group or, alternatively, from a thiol group.

The acidic compound may be a low molecular compound or a polymeric compound and may comprise, for example, up to 1000, notably up to 500, preferably up to 100 groups selected from a hydroxy group, a thiol group, an imide group, a carboxylic acid group or an acidic carbon-hydrogen group.

In a preferred embodiment, the acidic compound is an organic compound comprising 1 to 10, notably 1 to 6 groups, more preferably 1 to 4 and most preferably 1 or 2 groups selected from a hydroxy group, a thiol group, an imide group, a carboxylic acid group or an acidic carbon-hydrogen group.

In a preferred embodiment, the organic compound comprises either hydroxy groups, either thiol groups, either imide groups, either carboxylic acid groups or either acidic carbon-hydrogen groups and does not comprise any combinations thereof.

The organic compound may comprise additional functional groups and may comprise other heteroatoms than oxygen and sulfur. The organic compound may, for example, comprise carbonyl groups, thioether groups or ether groups.

In a preferred embodiment, the organic compound does not comprise nitrogen atoms in the additional functional groups.

In a particularly preferred embodiment, the organic compound does not comprise other heteroatoms than oxygen or sulfur.

In a more preferred embodiment, the organic compound does not comprise other additional functional groups than carbonyl groups, thioether groups or ether groups.

The organic compound may be an aliphatic or aromatic compound or a compound that comprises both, aliphatic and aromatic groups.

Preferably, the organic compounds have a number average molecular weight Mn of up to 1,000,000 g/mol, notably up 100,000 g/mol and more preferably of up to 10,000 g/mol, as determined by GPC against polystyrene as standard.

Particularly preferred organic compounds are non-polymeric compounds having a defined molecular weight of up to 5000 g/mol, notably of up to 1000 g/mol.

Preferred examples of organic compounds are aromatic or aliphatic monohydroxy compounds or aromatic or aliphatic monothiols, aromatic or aliphatic dihydroxy compounds or aromatic or aliphatic dithiols.

Most preferred examples of organic compounds are compounds with hydroxy or thiol groups that are directly bonded to an aromatic ring system.

The base may be an organic or inorganic base. An organic base is, for example, a tertiary amine.

Preferably, the base is an alkali hydroxide or an earth alkali hydroxide.

Most preferably, the base is an alkali hydroxide, notably sodium hydroxide or potassium hydroxide.

The organic compound and the base form a salt, wherein the organic compound is the anion and the base the cation.

To the Compound of Formula (I)

The salt of the acidic compound and of the base is reacted with a compound of formula (I)

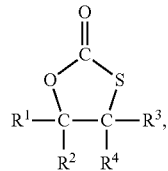

wherein one of the groups $R^1$ to $R^4$ is a group of formula (II)

-A-X with A representing an organic group with at least one carbon atom and X representing a halide, and the remaining groups $R^1$ to $R^4$ independently from each other represent hydrogen or an organic group with 1 to 50 carbon atoms.

The term "halide", as used herein for X, is the trivial name of a covalently bonded halogen atom, preferably a Cl atom.

Preferably, one of the groups $R^1$ to $R^4$ is a group of formula (II), and the remaining groups $R^1$ to $R^4$ independently from each other represent hydrogen or an organic group with from 1 to 10 carbon atoms. The organic group is preferably a hydrocarbon group, notably an alkyl group.

More preferably, one of the groups $R^1$ to $R^4$ is a group of formula (II), and the remaining groups $R^1$ to $R^4$ are hydrogen.

Preferably, A is an alkylene group with 1 to 10 carbon atoms, notably with 1 to 4 carbon atoms, and most preferably A is methylene.

Preferably, X is a chloride.

The term "chloride", as used herein for X, is the trivial name of a covalently bonded Cl atom.

Preferably, $R^1$ is the group of formula (II).

A most preferred compound of formula (I) is a compound of formula (III)

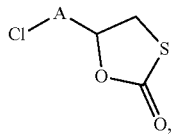

wherein A has the above meaning, i.e., representing an organic group with at least one carbon atom, preferably A is an alkylene group with 1 to 10 carbon atoms, notably with 1 to 4 carbon atoms, and most preferably A is methylene.

A most preferred compound of formula (III) is, for example, 5-(chloromethyl)-1,3-oxathiolane-2-one.

To the Synthesis of Compound of Formula (I)

The compound of formula (I) is a compound with a five membered, cyclic monothiocarbonate ring system.

Various methods for the synthesis of compounds with a monothiocarbonate ring system are described in the state of the art.

According to U.S. Pat. Nos. 3,072,676 and 3,201,416 ethylene monothiocarbonates may be prepared by a two-step-process. In a first step mercaptoethanol and chlorocarboxylates are reacted to give hydroxyethylthiocarbonate, which is heated in the second step in the presence of a metal salt catalyst to the ethylene monothiocarbonate.

According U.S. Pat. No. 3,517,029 alkylene monothiocarbonates are obtained by reacting mercaptoethanol and a carbonate diester in the presence of a catalytically active salt of thorium.

According to the process disclosed in U.S. Pat. No. 3,349,100 alkylene monothiocarbonates are obtained by reacting an epoxide with carbonyl sulfide. The availability of carbonyl sulfide is limited. Yields and selectivities of alkylene monothiocarbonates obtained are low.

A synthesis using phosgene as starting material is known from U.S. Pat. No. 2,828,318. Phosgene is reacted with hydroxymercaptanes. Yields of monothiocarbonates are still low, and by-products from polymerization are observed.

A preferred process for the preparation of a compound with a five membered, cyclic monothiocarbonate ring system is a process, wherein
   a) a compound with an epoxy group (shortly referred to as epoxy compound) is used as starting material,
   b) the compound is reacted with phosgene or an alkyl chloroformate thus giving an adduct, and
   c) the adduct is reacted with a compound comprising anionic sulfur to give the compound with a five-membered cyclic monothiocarbonate group.

This process is in detail described in WO 2019/034469 A1.

To the Process

In a first step a salt of an acidic compound and of a base may be formed separately, and the salt obtained is then reacted with the compound of formula (I).

Alternatively, the acidic compound may be reacted with the compound of formula (I) in the presence of the base, and the salt is formed in situ. In this alternative, the base is preferably used in an amount of 0.1 to 5 mols, more preferably in an amount of 0.5 to 2 mols per 1 mol of the groups selected from hydroxy, thiol, imide and carboxylic acid groups.

The acidic compound may also be formed in situ, for example, organic compounds with thiol groups may be formed via a Michael addition reaction by reacting hydrogen sulfide with a compound having an unsaturated bond.

The reaction may be performed in the presence of a solvent. Suitable solvents are polar solvents, such as dimethylformamide. Ionic liquids may also be used as solvents.

The salt of the acidic compound, respectively hydrogen sulfide or the organic compound, may be reacted with the compound of formula (I) in any molar relationship. In order to avoid large amounts of unreacted starting materials, 0.5 to 2 mols of the salt, respectively the organic compound may be reacted with 1 mol of the compound of formula (I).

Preferably, 0.8 to 1.3 mols of the salt, respectively of hydrogen sulfide or of the organic compound, are reacted with 1 mol of the compound of formula (I).

The reaction is preferably performed at elevated temperatures, notably at temperatures from of 50 to 150° C.

The reaction mixture may comprise additives, such as stabilizers or biocides, for example, phenothiazine. Starting materials that are offered in the market may already comprise stabilizers or biocides.

In the reaction, a phase transfer catalyst may be used. Suitable phase transfer catalysts may be, for example, quaternary ammonium salts, such as $NMe_4Cl$.

In the reaction, a ring opening of the cyclic monothiocarbonate is not observed. Instead, a substitution reaction occurs under formation of the desired compound with at least one cyclic monothiocarbonate group and a salt of the halide. The latter is, for example, sodium chloride in case that X in formula (II) is chloride, and sodium hydroxide has been used as base. This salt may be separated from the product mixture by usual means, for example, filtration.

The product may be further purified, for example, by distillation.

In a further aspect, the invention relates to compounds obtainable by reacting the salt of an acidic compound selected from hydrogen sulfide or an organic compound comprising at least one thiol group with a compound of formula (III)

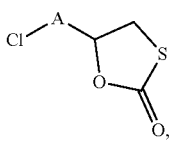

wherein A is an organic group with at least one carbon atom, preferably an alkylene group with 1 to 10 carbon atoms.

Further, the invention relates to compounds obtainable by reacting the salt of an acidic compound selected from hydrogen sulfide or an organic compound comprising at least one thiol group with 5-(chloromethyl)-1,3-oxathiolane-2-one.

Further, the invention relates to compounds obtainable by reacting the salt of an organic compound comprising at least one imide group with a compound of formula (III)

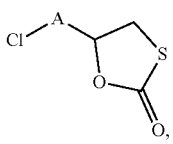

wherein A is an organic group with at least one carbon atom, preferably an alkylene group with 1 to 10 carbon atoms.

Further, the invention relates to compounds obtainable by reacting the salt of an organic compound comprising at least one imide group with 5-(chloromethyl)-1,3-oxathiolane-2-one.

The product obtained in case of hydrogen sulfide as starting material may have one or two cyclic monothiocarbonate groups, preferably two cyclic monothiocarbonate groups, due to two acid hydrogen atoms of hydrogen sulfide.

The product obtained in case of an organic compound as starting material is an organic compound now being modified by at least one cyclic monothiocarbonate functionality.

In case of an organic compound with hydroxy groups, a compound with ether groups and cyclic monothiocarbonate groups is formed as product.

In case of an organic compound with thiol groups, a compound with thioether groups and cyclic monothiocarbonate groups is formed as product.

In case of an organic compound with imide groups, a compound with substituted imide groups and cyclic monothiocarbonate groups is formed as product.

In case of an organic compound with carboxylic groups, a compound with ester groups and cyclic monothiocarbonate groups is formed as product.

Particularly preferred compounds obtained by the process are compounds that are obtainable by reacting the salt of an organic compound comprising at least one thiol group, preferably one or two thiol groups, with a compound of formula (III)

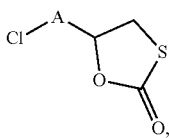

whereby the compound of formula (III) is preferably 5-(chloromethyl)-1,3-oxathiolane-2-one.

Particularly preferred compounds obtained by the process are also compounds obtainable by reacting the salt of an organic compound comprising at least one imide group, preferably one or two imide groups, with a compound of formula (III)

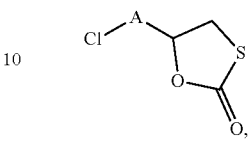

whereby the compound of formula (III) is preferably 5-(chloromethyl)-1,3-oxathiolane-2-one.

Examples of compounds with one thioether group and one cyclic monothiocarbonate group are the following compounds

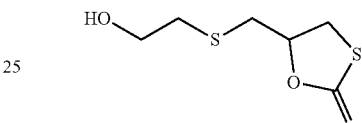

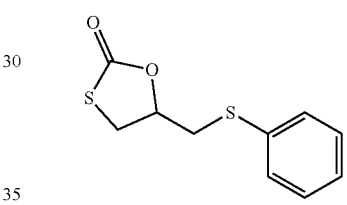

A compound with one thioether group and two cyclic monothiocarbonate group is obtained by reacting the compound of formula (III) with hydrogen sulfide:

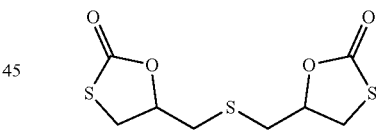

Examples of compounds with two thioether groups and two cyclic monothiocarbonate groups are

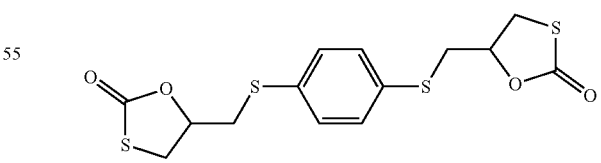

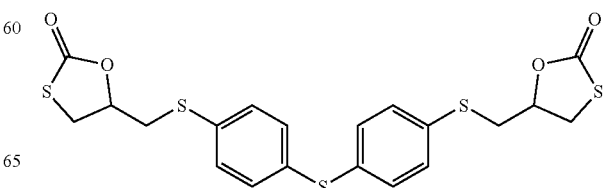

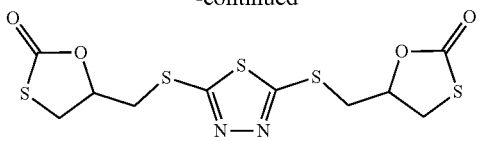

Examples of compounds with one substituted imide group and one cyclic monothiocarbonate group are the following compounds:

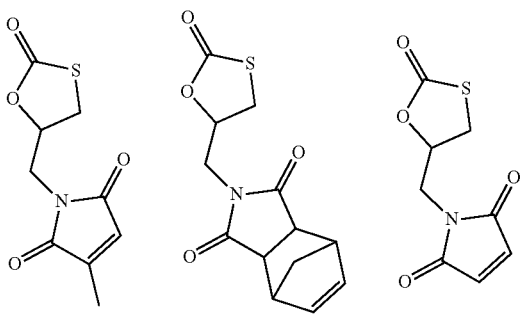 [SMILES: CC1=CC(=O)N(CC2CSC(=O)O2)C1=O ; O=C1OC(CN2C(=O)C3C4C=CC(C4)C3C2=O)CS1 ; O=C1OC(CN2C(=O)C=CC2=O)CS1]

An example of a compound with two substituted imide groups and two cyclic monothiocarbonate groups is the following compound:

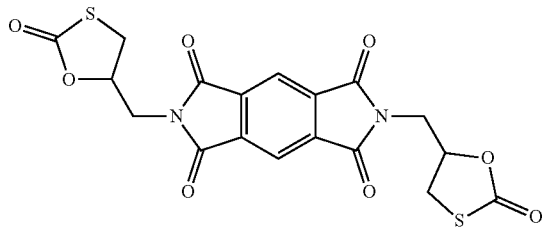 [SMILES: O=C1OC(Cn2c(=O)c3cc4c(=O)n(CC5CSC(=O)O5)c(=O)c4cc3c2=O)CS1]

An example of a compound with three substituted imide groups and three cyclic monothiocarbonate groups is the following compound

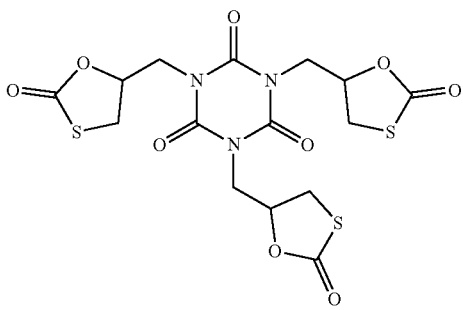 [SMILES: O=C1OC(Cn2c(=O)n(CC3CSC(=O)O3)c(=O)n(CC3CSC(=O)O3)c2=O)CS1]

The process of this invention is an easy process to introduce monothiocarbonate functionality in other chemical compounds, including polymers. The process is economic and does not involve the use or formation of any harmful materials. The process is very selective. In the process, ring opening reactions of the compound of formula (I) are not observed.

EXAMPLES

GC analysis: Agilent Technologies 7890 A Network GC System
Column: DB1 (Agilent) 30 m, Ø 0.25 mm, film thickness 1 μm;
Carrier gas He; flow 1.0 mL/min; split ratio: 50:1
T-program: 50° C.-300° C., with ramp rate of 10° C./min; 30 min isotherm
Temperature (injection system) 250° C.

Synthesis Example 5-(Chloromethyl)-1,3-oxathiolane-2-one was used as compound of formula (III). 5-(Chloromethyl)-1,3-oxathiolane-2-one was prepared according to WO 2019/034469 A1 as follows:

Into a 2 L stirred tank glass reactor equipped with two condensers (−30° C. and −78° C. (dry ice)) phosgene dip pipe and internal thermometer 594 g (6.41 mol, 1.00 eq.) of epichlorohydrin were introduced under an atmosphere of nitrogen. After the addition of the starting material the cooling of the tank reactor was turned on and was adjusted to 15° C. After the reactor reached this temperature, 17.8 g (0.0640 mol, 1.00 mol %) of tetrabutylammonium chloride (TBACl) were added. After solvation of the TBACl gaseous phosgene (overall 821 g, 8.3 mol, 1.29 eq.) was added to the reactor via the dip pipe. The temperature of the reaction mixture was continuously monitored and was kept below 25° C. by carefully adjusting the rate of the phosgene addition. Overall the phosgene addition took approximately 9 hours. After the phosgene addition was completed the initial cooling of the reactor was turned off, and the reactor was allowed to slowly reach room temperature (ca. 25° C.). Afterwards the reaction mixture was stirred at room temperature for 2 hours. Finally, the reaction mixture was stripped, with nitrogen at room temperature, phosgene-free overnight. The resulting colorless, slightly viscous oil (1214 g, 6.34 mol, 99% yield, regioisomeric purity >95%) was directly used, without further purification, for the thiocarbonate formation.

The respective β-chloroalkyl chloroformate from above (50 g) and dichloromethane (50 mL) were placed in a 500 mL 4 neck round bottom flask equipped with a KPG crescent stirrer, dropping funnel, thermometer and a reflux condenser. The solution was cooled down to 0° C. with an ice bath before Na₂S (1 eq., 15 wt % aqueous solution) was slowly added, maintaining the temperature at 5° C. After the complete addition the ice bath was removed, and the reaction mixture was allowed to warm to room temperature. After stirring for 2 hours the phases were separated, and the aqueous phase was extracted with dichloromethane (2×50 mL). The solvent was removed from the combined organic phases under reduced pressure, and the residual liquid was purified by distillation, yielding the desired cyclic thiocarbonate 5-(chloromethyl)-1,3-oxathiolane-2-one in 77% yield.

Example 1

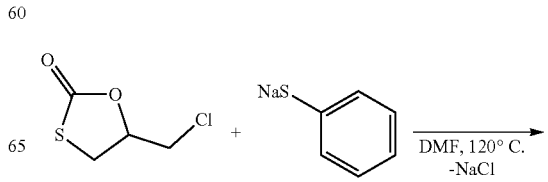

-continued

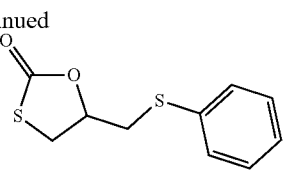

Sodium thiophenolate (0.61 g, 5 mmol) was dissolved in dimethylformamide (DMF) (6 g) and 5-(chloromethyl)-1,3-oxathiolane-2-one (0.76 g, 5 mmol) was added. The solution was heated to 120° C. and stirred for 2 hours.

Based on GC analysis 75% conversion of the 5-(chloromethyl)-1,3-oxathiolane-2-one was achieved, and 5-(phenylsulfanylmethyl)-1,3-oxathiolane-2-one ($C_{10}H_{10}S_2O_2$) was afforded in 67% yield.

GC-MS analysis: GC (Agilent 7890 A) coupled with MS (Agilent 5975 C) for EI and CI ionisation GC Column: DB1701, 30 m, Ø 0.25 mm, film thickness 1 μm;

Carrier gas He; flow 1.2 mL/min; split ratio: 30:1

T-program: 50° C.-280° C., with ramp rate of 20° C./min; 30 min isotherm

Temperature (injection system) 250° C.

MS/EI, mass range 25-785 amu; ionization energy 70 eV

MS/CI, mass range 55-815 amu

The molecular weight of 226 was determined by EI and CI ionization. The structure of 5-(phenylsulfanylmethyl)-1,3-oxathiolane-2-one was confirmed by $^1$H-NMR ($CD_2Cl_2$).

Example 2

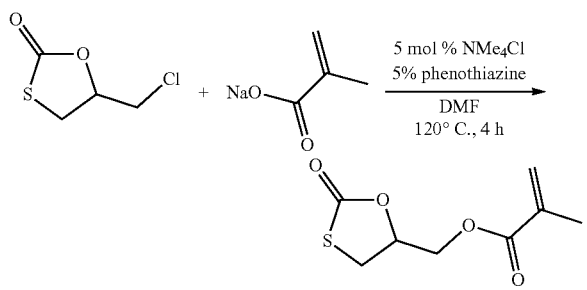

Sodium methacrylate (3.6 g, 33 mmol), tetramethylammonium chloride (0.46 g, 5 mol %) and phenothiazine (5.4 mg, 0.15 wt %) were dissolved in DMF (20 g) and 5-(chloromethyl)-1,3-oxathiolane-2-one (5 g, 33 mmol) was added. The solution was heated to 120° C. and stirred for 4 hours.

Based on GC analysis (2-oxo-1,3-oxathiolane-5-yl) methyl 2-methylprop-2-enoate was afforded in 48% yield.

Example 3

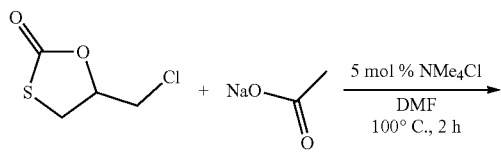

-continued

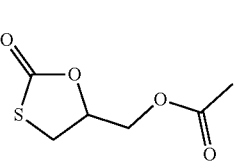

Sodium acetate (2.7 g, 33 mmol) and tetramethylammonium chloride (0.46 g, 5 mol %) were dissolved in DMF (20 g), and 5-(chloromethyl)-1,3-oxathiolane-2-one (5 g, 33 mmol) was added. The solution was heated to 100° C. and stirred for 2 hours.

Based on GC analysis (2-oxo-1,3-oxathiolane-5-yl) methyl-acetate was afforded in 23% yield.

Example 4

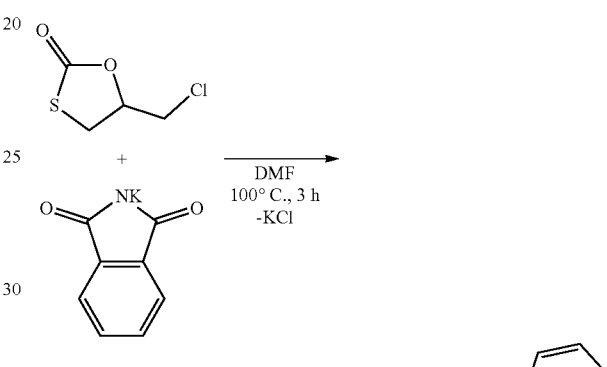

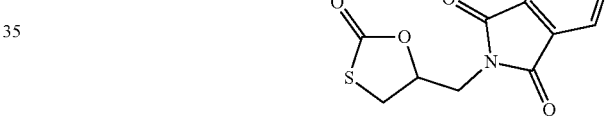

Potassium phthalimide (0.93 g, 5 mmol) was dissolved in dimethylformamide (DMF) (6 g) and 5-(chloromethyl)-1,3-oxathiolane-2-one (0.76 g, 5 mmol) was added. The solution was heated to 100° C. and stirred for 3 hours.

Based on GC analysis the product was afforded in 22% yield.

The invention claimed is:

1. A process for the preparation of a compound comprising at least one cyclic monothiocarbonate group, the process comprising:

reacting a salt, formed of an acidic compound with at least one acidic hydrogen atom and a base, with a compound of formula (I)

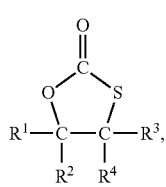

wherein one of the groups $R^1$ to $R^4$ is a group of formula (II)

-A-X with A representing an organic group with at least one carbon atom and X representing a halide, and wherein the remaining groups $R^1$ to $R^4$ independently from each other represent hydrogen or an organic group with 1 to 50 carbon atoms.

2. The process according to claim 1, wherein the acidic compound is hydrogen sulfide or an organic compound with at least one group selected from the group consisting of a hydroxy group, a thiol group, an imide group, a carboxylic acid group, and an acidic carbon-hydrogen group.

3. The process according to claim 1, wherein the acidic compound is an organic compound with one to ten groups selected from the group consisting of a hydroxy group, a thiol group, an imide group, a carboxylic acid group, and an acidic carbon-hydrogen group.

4. The process according to claim 2, wherein the acidic compound is the organic compound, and wherein the organic compound has a molecular weight of at maximum 1000 g/mol.

5. The process according to claim 2, wherein the acidic compound is the organic compound, and wherein the organic compound does not comprise other heteroatoms than oxygen or sulfur.

6. The process according to claim 2, wherein the acidic compound is the organic compound, and wherein the organic compound further comprises carbonyl groups, thioether groups or ether groups.

7. The process according to claim 1, wherein the base is an alkali hydroxide.

8. The process according to claim 1, wherein one of the groups $R^1$ to $R^4$ in formula (I) is a group of formula (II), and the remaining groups $R^1$ to $R^4$ are hydrogen.

9. The process according to claim 1, wherein A in formula (II) is an alkylene group with 1 to 10 carbon atoms.

10. The process according to claim 1, wherein X in formula (II) is chloride.

11. The process according to claim 1, wherein the compound of formula (I) is a compound of formula (III)

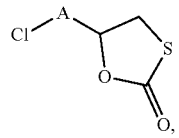

wherein A is an organic group with at least one carbon atom.

12. The process according to claim 1, wherein the salt of the acidic compound and the base is formed separately, and the salt obtained is then reacted with the compound of formula (I).

13. The process according to claim 1, wherein the acidic compound is reacted with the compound of formula (I) in the presence of the base, and the salt is formed in situ.

14. The process according to claim 11, wherein A is an alkylene group with 1 to 10 carbon atoms.

* * * * *